United States Patent
Harada et al.

(10) Patent No.: US 10,121,377 B2
(45) Date of Patent: Nov. 6, 2018

(54) INFRASTRUCTURE INSPECTION APPARATUS, INFRASTRUCTURE INSPECTION METHOD, AND INFRASTRUCTURE INSPECTION SYSTEM

(71) Applicant: Panasonic Intellectual Property Corporation of America, Torrance, CA (US)

(72) Inventors: Naoyuki Harada, Osaka (JP); Masahiko Saito, Osaka (JP); Yohei Nakata, Osaka (JP); Kazuma Takeuchi, Osaka (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 0 days.

(21) Appl. No.: 15/457,372

(22) Filed: Mar. 13, 2017

(65) Prior Publication Data

US 2017/0287333 A1 Oct. 5, 2017

(30) Foreign Application Priority Data

Apr. 1, 2016 (JP) .................................. 2016-074663

(51) Int. Cl.
*G08G 1/16* (2006.01)
*G01N 21/88* (2006.01)
(Continued)

(52) U.S. Cl.
CPC ............. *G08G 1/164* (2013.01); *B60W 30/16* (2013.01); *G01M 5/00* (2013.01);
(Continued)

(58) Field of Classification Search
CPC .... G01M 5/00; G01M 5/0008; G01M 5/0033; G01M 5/0041; G01M 5/005; G01M 5/0075; G08G 1/0116
See application file for complete search history.

(56) References Cited

U.S. PATENT DOCUMENTS 9,417,154 B2* 8/2016 Muncy ................ G01M 5/0008
9,834,212 B2* 12/2017 Park ...................... B60W 30/12
(Continued)

FOREIGN PATENT DOCUMENTS

| DE | 102013213583 A1 | 1/2015 |
| JP | 2001-283380 A | 10/2001 |
| JP | 2007-212309 | 8/2007 |

OTHER PUBLICATIONS

The Extended European Search Report dated Feb. 7, 2018 for the related European Patent Application No. 17162504.9.

*Primary Examiner* — Thomas G Black
*Assistant Examiner* — Sara J Lewandroski
(74) *Attorney, Agent, or Firm* — Greenblum & Bernstein, P.L.C.

(57) ABSTRACT

An inspection method includes, with a sensor mounted in an infrastructure, measuring drive assisting information that is to be used to perform a drive assisting operation of a target vehicle that uses the infrastructure, transmitting the drive assisting information to the target vehicle, receiving, from the target vehicle, information of the infrastructure measured by the target vehicle, and inspecting the infrastructure using the information of the infrastructure.

9 Claims, 5 Drawing Sheets

(51) Int. Cl.
   *G05D 1/02*      (2006.01)
   *G08G 1/01*      (2006.01)
   *G08C 17/02*     (2006.01)
   *B60W 30/16*     (2012.01)
   *G01M 5/00*      (2006.01)
   *G06K 9/00*      (2006.01)
   *G08G 1/04*      (2006.01)
   *G08G 1/052*     (2006.01)

(52) U.S. Cl.
   CPC ....... *G01N 21/8851* (2013.01); *G05D 1/0285* (2013.01); *G06K 9/00785* (2013.01); *G08C 17/02* (2013.01); *G08G 1/0104* (2013.01); *G08G 1/0112* (2013.01); *G08G 1/0125* (2013.01); *G08G 1/04* (2013.01); *G08G 1/052* (2013.01)

(56) References Cited

U.S. PATENT DOCUMENTS

| | | | |
|---|---|---|---|
| 2006/0276985 A1* | 12/2006 | Xu | G01C 7/04 702/81 |
| 2010/0082244 A1* | 4/2010 | Yamaguchi | G08G 1/163 701/532 |
| 2011/0130894 A1* | 6/2011 | Kim | G05D 1/0282 701/2 |
| 2015/0013465 A1* | 1/2015 | Godfrey | B61L 23/044 73/655 |
| 2016/0011124 A1* | 1/2016 | Kruglick | G01C 21/26 324/637 |
| 2017/0025013 A1* | 1/2017 | Lee | G06K 9/00798 |
| 2017/0278391 A1* | 9/2017 | Ono | G08G 1/0965 |

* cited by examiner

INFRASTRUCTURE INSPECTION APPARATUS, INFRASTRUCTURE INSPECTION METHOD, AND INFRASTRUCTURE INSPECTION SYSTEM

BACKGROUND

1. Technical Field

The present disclosure relates to an infrastructure inspection apparatus, an infrastructure inspection method, and an infrastructure inspection system, each configured to inspect an infrastructure.

2. Description of the Related Art

Infrastructures, such as tunnels, roads, and bridges age with time. Such aging infrastructures are to be inspected at lower costs with higher frequency. Serious accidents may be controlled by finding a fault in the infrastructure through early inspection.

Equipping a vehicle with a function that assists a driver in driving the vehicle (hereinafter referred to as a drive assisting function) has been started recently. A vehicle having the drive assisting function includes a sensor that measures a surrounding state, and a technique of using such a sensor to acquire data that is used to inspect the infrastructure is disclosed in Japanese Unexamined Patent Application Publication No. 2007-212309.

If the disclosed technique measures an infrastructure with a drive assisting sensor, a drive assisting capability may be lowered. For example, if a wall surface of a tunnel is photographed using a camera that is intended to photograph an obstacle present ahead to detect a possible collision, the capability of controlling collision against the obstacle ahead may be decreased. Vehicles that participate in the measurement of the infrastructure are thus limited.

SUMMARY

One non-limiting and exemplary embodiment provides an infrastructure inspection apparatus that inspects an infrastructure using information of the infrastructure measured by a vehicle while controlling a decrease in a drive assisting capability of the vehicle.

In one general aspect, the techniques disclosed here feature an infrastructure inspection apparatus. The infrastructure inspection apparatus includes a sensor that measures drive assisting information that is used to perform a driving assisting operation of a target vehicle that uses an infrastructure, a transmitter that transits the drive assisting information to the target vehicle, a receiver that receives, from the target vehicle, information of the infrastructure measured by the target vehicle, and circuitry which performs operations, the operations including inspecting the infrastructure using the received information of the infrastructure.

It should be noted that general or specific embodiments may be implemented as a system, a method, an integrated circuit, a computer program, a computer-readable storage medium such as a compact-disk read-only memory (CD-ROM), or any selective combination thereof.

The infrastructure inspection apparatus of an embodiment of the disclosure inspects an infrastructure using information of the infrastructure measured by a vehicle while controlling a decrease in the drive assisting capability of the vehicle.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

An embodiment is described with reference to the drawings.

The embodiment described below indicates a general or specific example. Values, shapes, materials, elements, layout positions of the elements, connection configurations, steps, and the order of the steps described below are described for exemplary purposes only, and are not intended to limit the scope of the claims. From among the elements described in the embodiment, elements that are not described in independent claims indicating a generic concept are regarded as optional elements.

Each drawing is diagrammatical, and is not necessarily drawn to exact scale.

Embodiment

Configuration of Infrastructure Inspection System

Figure 1:
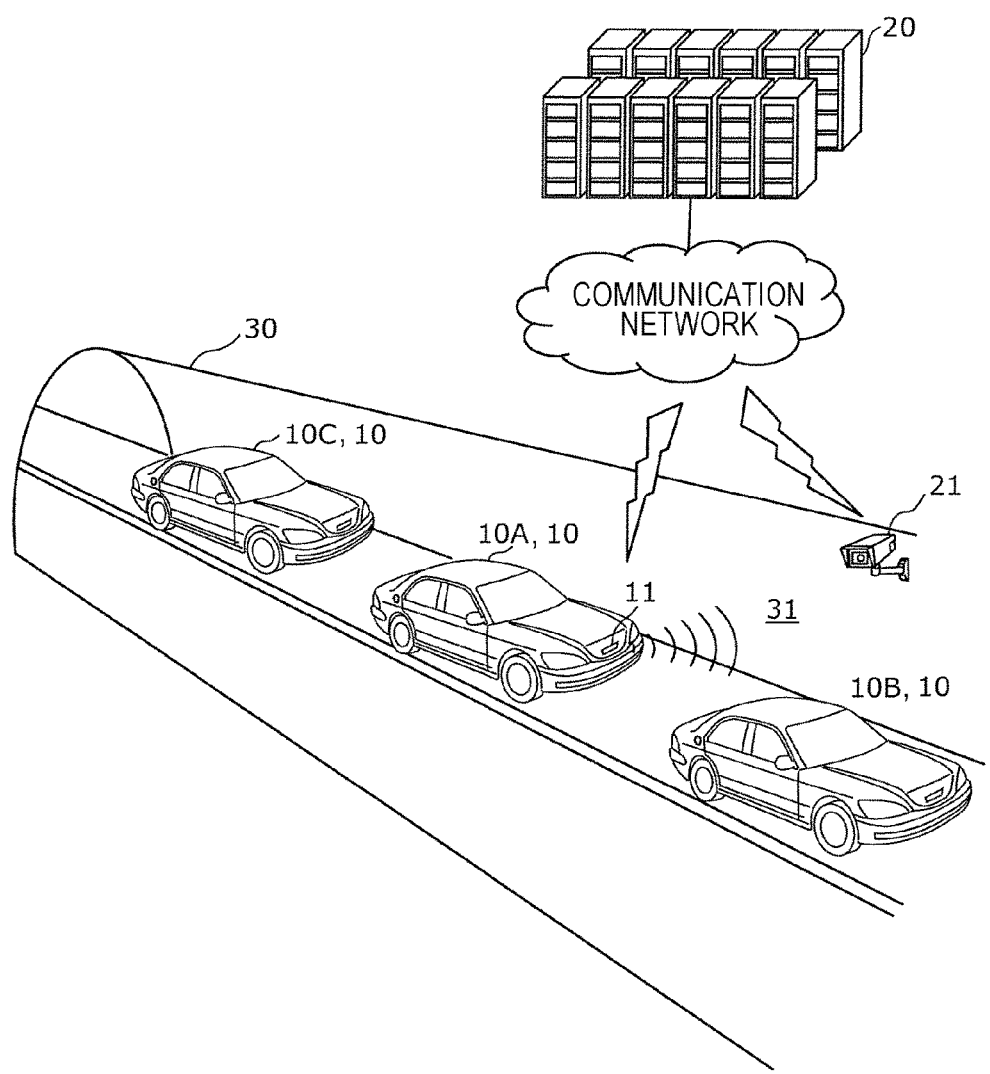
FIG. 1 generally illustrates an infrastructure inspection system of an embodiment.

The configuration of the infrastructure inspection system is described with reference to FIG. 1. FIG. 1 diagrammatically illustrates the infrastructure inspection system of the embodiment. Referring to FIG. 1, a target vehicle 10A measures a wall surface 31 of a tunnel 30 using a sensor 11 while running through the tunnel 30, and transmits measurement results to a server 20. A sensor 21 mounted in the tunnel 30 measures information of multiple vehicles 10 running in the tunnel 30 (the target vehicle 10A, a forward vehicle 10B, and a backward vehicle 10C). The measurement results of the sensor 21 are transmitted to the target vehicle 10A.

The target vehicle 10A has a drive assisting function. For example, the target vehicle 10A has functions for collision control (automatic braking), uniform velocity cruising (auto-cruising), lane-keep assisting, and fully automated driving.

A sensor 11, mounted on the target vehicle 10A, measures an external state. More specifically, the sensor 11 may be a stereo camera, a laser range finder, or a sonar. The sensor 11 measures a range between the target vehicle 10A and the forward vehicle 10B or the backward vehicle 10C in the vicinity of the target vehicle 10A. The sensor 11 also photographs the wall surface, and the road surface, and a device (such as lamps, or a blower) of the tunnel 30.

The server 20 is an information processing apparatus that inspects the tunnel 30. More specifically, the server 20 is a cloud server. The server 20 is connected to the target vehicle 10A and the sensor 21 via a communication network.

The sensor 21, mounted within the tunnel 30, measures information of multiple vehicles 10 running in the tunnel 30. More specifically, the sensor 21 includes a speed sensor that detects the velocity of a vehicle, and a camera that photographs a license plate of the vehicle.

The tunnel 30 is an example of the infrastructure, which is used by vehicles. More specifically, the tunnel 30 is a structure that penetrates the ground, and vehicles run through the tunnel 30.

Functional Configuration of Infrastructure Inspection System

Figure 2:
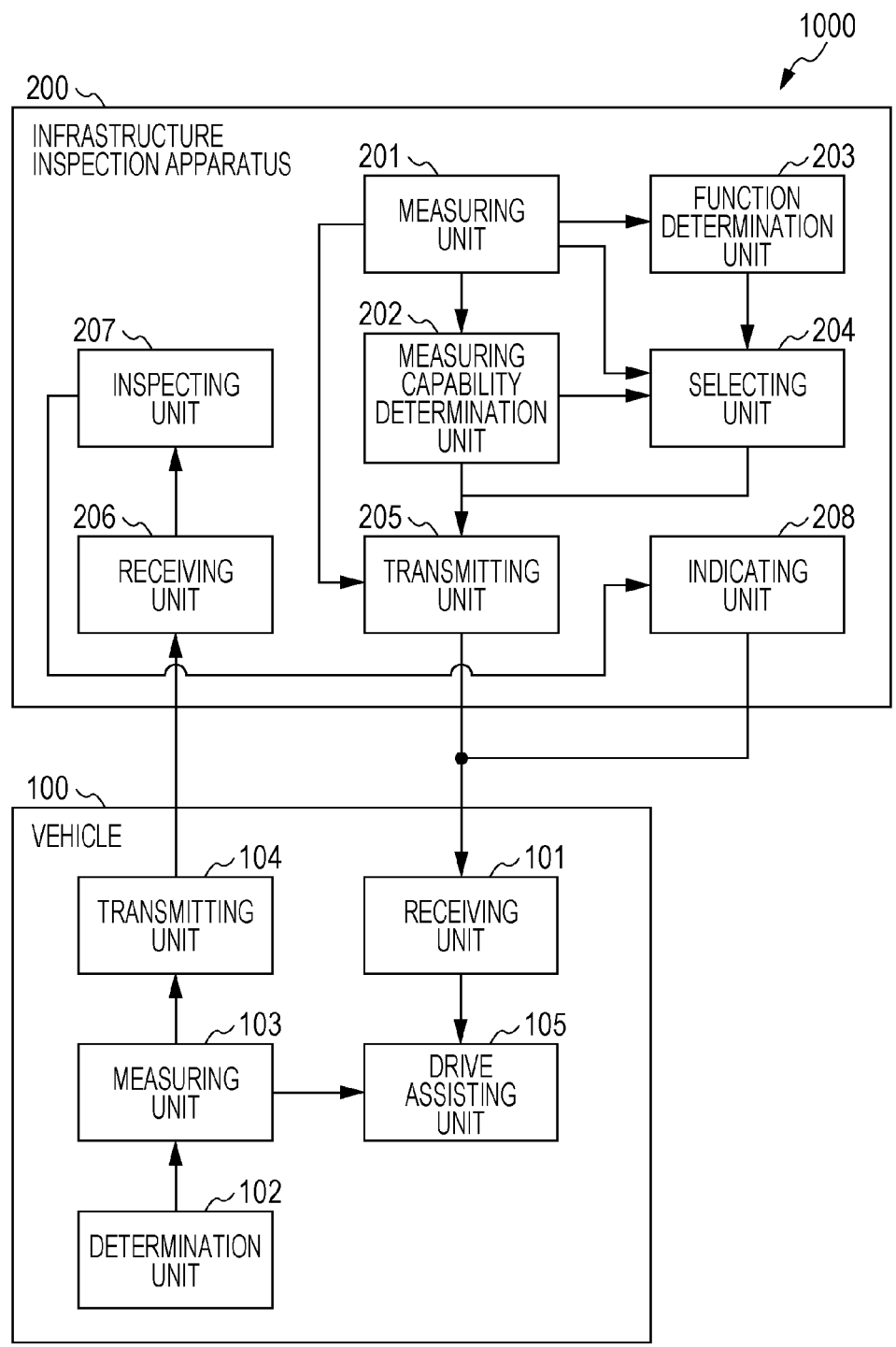
FIG. 2 is a functional block diagram of the infrastructure inspection system of the embodiment.

The functional configuration of an infrastructure inspection system 1000 is described with reference to FIG. 2. The infrastructure inspection system 1000 of FIG. 2 includes a vehicle 100 and an infrastructure inspection apparatus 200. Elements included in the infrastructure inspection system 1000 are described in detail.

Configuration of Vehicle

The configuration of the vehicle 100 is described first. The vehicle 100 has the drive assisting function, and corresponds to the target vehicle 10A of FIG. 1. The vehicle 100 includes a receiving unit 101, a determination unit 102, a measuring unit 103, a transmitting unit 104, and a drive assisting unit 105.

The receiving unit 101 includes a radio communication adapter, and receives a variety of information from the infrastructure inspection apparatus 200 via radio communication (such as using a local area network (LAN)). When the measuring unit 103 described below measures the information of the infrastructure, the receiving unit 101 receives from the infrastructure inspection apparatus 200 drive assisting information for use in a drive assisting operation of the vehicle 100 (second drive assisting information). The receiving unit 101 may also receive from the infrastructure inspection apparatus 200 an indication of a measurement point where the information of the infrastructure is measured.

The drive assisting information includes at least position information or velocity information of at least one vehicle that uses the infrastructure. The drive assisting information may further include identity information of at least one vehicle. The drive assisting information may further include position information of a border of a lane, map information, and traffic control information.

The determination unit 102 determines whether to permit the information of the infrastructure to be measured. More specifically, the determination unit 102 determines whether to permit the information of the infrastructure to be measured in response to an input from a driver of the vehicle 100. For example, if the driver touches a permit button displayed on a touchscreen (not illustrated) mounted on the vehicle 100, the determination unit 102 determines that the measurement of the information of the infrastructure is to be permitted. The determination unit 102 may determine whether to permit the information of the infrastructure to be measured in response to a capability of the measuring unit 103. More specifically, if the measuring unit 103 has a capability of measuring the infrastructure, the determination unit 102 permits the information of the infrastructure to be measured. If the measuring unit 103 does not have the capability of measuring the infrastructure, the determination unit 102 inhibits the measurement of the information of the infrastructure.

In response to the drive assisting information received from the infrastructure inspection apparatus 200, the determination unit 102 may determine whether to permit the information of the infrastructure to be measured. More specifically, if the second drive assisting information received from the infrastructure inspection apparatus 200 is substitutable for first drive assisting information measured by the measuring unit 103, the determination unit 102 permits the information of the infrastructure to be measured. If the second drive assisting information is not substitutable for the first drive assisting information, the determination unit 102 inhibits the measurement of the information of the infrastructure. In other words, if the drive assisting capability of the vehicle 100 is not lowered, the measurement of the information of the infrastructure may be permitted.

If the vehicle 100 participates in a service for the measurement of the infrastructure, the determination unit 102 may permit the information of the infrastructure to be measured. For example, such a service may include a reduced rate for expressway toll as an incentive to the measurement of the infrastructure.

The measuring unit 103 corresponds to the sensor 11 of FIG. 1, and measures the information of the infrastructure that the vehicle 100 uses, and the drive assisting information for use in the drive assisting of the vehicle 100. More specifically, the measuring unit 103 selectively performs multiple measurement modes, including a first measurement mode to measure the drive assisting information and a second measurement mode to measure the information of the infrastructure. The first measurement mode is a standard measurement mode for driving assisting. The second measurement mode is a special measurement mode to inspect the infrastructure. Note that the drive assisting information may be measured in addition to the information of the infrastructure in the second measurement mode. The multiple measurement modes may further include another measurement mode in addition to the first and second measurement modes. For example, the measurement modes may include measurement modes for drive assisting, such as a measurement mode for fully automated driving, and a measurement mode for collision control.

If the measuring unit 103 is a range finder (laser range finder) to measure a range in a predetermined sector from the vehicle 100 for collision control purposes, the center direction of the measurement sector (sector in a predetermined direction) of the measuring unit 103 is approximately aligned with the direction to the front of the vehicle 100 in the first measurement mode, and the center direction of the measurement sector of the measuring unit 103 is shifted from the front direction of the vehicle 100 to the direction to the infrastructure in the second measurement mode. As a result, the range between the vehicle 100 and an object present straight ahead of the vehicle 100 is measured in the first measurement mode, and the range between the vehicle 100 and the infrastructure is mainly measured in the second measurement mode. The front direction of the vehicle 100 is a forward direction in which the vehicle 100 is running straight.

If the measuring unit 103 is a range finder (or a laser rangefinder) that measures a range within a circle centered on the vehicle 100 for fully automated driving, a measurement accuracy is set to be generally uniform within the circle in the first measurement mode, and the measurement accuracy is set to be higher in the direction to the infrastructure than in other directions in the second measurement mode. More specifically, in the second measurement mode, measurement resolution is set to be fine in the direction to the infrastructure and set to be coarse in the other directions.

If the determination unit 102 permits the information of the infrastructure to be measured, the measuring unit 103 measures the information of the infrastructure. On the other hand, if the determination unit 102 does not permit the information of the infrastructure to be measured, the measuring unit 103 measures the drive assisting information for use in the drive assisting operation of the vehicle 100 (the first drive assisting information). In other words, if the determination unit 102 permits the information of the infrastructure to be measured, the measuring unit 103 operates in the second measurement mode, and if the determination unit 102 does not permit the information of the infrastructure to be measured, the measuring unit 103 operates in the first measurement mode.

When the receiving unit 101 receives an indication of a measurement point from the infrastructure inspection apparatus 200, the measuring unit 103 measures the information of the infrastructure at the measurement point. For example, if a location of a given apparatus within the infrastructure is indicated as a measurement point, the measuring unit 103 measures information of the apparatus at the measurement point.

The transmitting unit 104, including a radio communication adapter, transmits a variety of information to the infrastructure inspection apparatus 200 via radio communication. More specifically, when the measuring unit 103 measures the information of the infrastructure, the transmitting unit 104 transmits the information of the infrastructure to the infrastructure inspection apparatus 200. Note that the transmitting unit 104 may transmit the information of the infrastructure to the infrastructure inspection apparatus 200 while or after the infrastructure is used. For example, the transmitting unit 104 may transmit the information of the infrastructure while the vehicle 100 is running in the tunnel 30 or after the vehicle 100 comes out of the tunnel 30.

If the measuring unit 103 measures the drive assisting information, the drive assisting unit 105 performs the drive assisting operation of the vehicle 100 in accordance with the drive assisting information measured by the measuring unit 103 (the first drive assisting information). If the measuring unit 103 measures the information of the infrastructure, the drive assisting unit 105 performs the drive assisting operation of the vehicle 100 in accordance with the drive assisting information received by the receiving unit 101 (the second drive assisting information). If the measuring unit 103 measures the drive assisting information (the first drive assisting information) together with the information of the infrastructure, the drive assisting unit 105 may perform the drive assisting operation of the vehicle 100 in accordance with both the first drive assisting information measured by the measuring unit 103 and the second drive assisting information received by the receiving unit 101.

The drive assisting operation is intended to mean that a driver is assisted in driving the vehicle 100 by automatically performing at least of one of an acceleration operation, a steering operation, and a braking operation of the vehicle 100.

If the receiving unit 101 receives the indication of the measurement point from the infrastructure inspection apparatus 200, the drive assisting unit 105 may perform the drive assisting operation of the vehicle 100 in response to the measurement point. In other words, the drive assisting unit 105 may perform the drive assisting operation of the vehicle 100 to cause the vehicle 100 to reach a location that is appropriate to measuring the information at the measurement point. More specifically, if the specified measurement point is on the wall surface of a second lane next to a first lane in which the vehicle 100 is currently running, the drive assisting unit 105 may cause the vehicle 100 to move from the first lane to the second lane.

Configuration of Infrastructure Inspection Apparatus

The configuration of the infrastructure inspection apparatus 200 is described below. The infrastructure inspection apparatus 200 inspects the infrastructure used by the vehicle 100. The infrastructure inspection apparatus 200 corresponds to the server 20 and the sensor 21 illustrated in FIG. 1. The infrastructure inspection apparatus 200 includes a measuring unit 201, a measuring capability determination unit 202, a function determination unit 203, a selecting unit 204, a transmitting unit 205, a receiving unit 206, an inspecting unit 207, and an indicating unit 208.

The measuring unit 201 corresponds to the sensor 21 of FIG. 1, and measures the drive assisting information (the second drive assisting information) for use in the drive assisting operation of the vehicle 100 using the infrastructure (the target vehicle 10A of FIG. 1, for example). For example, the measuring unit 201 measures information of at least one vehicle (multiple vehicles 10 of FIG. 1, for example) that uses the infrastructure. More specifically, the measuring unit 201 captures an image of at least one vehicle that uses the infrastructure, and recognizes identity information of each of at least one vehicle (such as a license plate) from the image. The measuring unit 201 also measures the position and velocity of at least one vehicle that uses the infrastructure.

The measuring capability determination unit 202 determines whether the vehicle 100 is capable of measuring the information of the infrastructure. More specifically, the measuring capability determination unit 202 acquires identity information of the vehicle 100 from the measuring unit 201, and references measurement capability information using the identity information. The measuring capability determination unit 202 thus determines whether the vehicle 100 is capable of measuring the information of the infrastructure. The measurement capability information defines a correspondence relationship between the identity information and measurement capability, and may be stored on a storage device (not illustrated). Based on information received from the vehicle 100, the measuring capability determination unit 202 may determine the measurement capability. Also, the measuring capability determination unit 202 may determine the measurement capability by recognizing the type of a sensor mounted on the vehicle 100 from the image of the vehicle 100.

The function determination unit 203 determines the drive assisting functions of the vehicle 100. The drive assisting functions are to assist the driver in driving the vehicle. For example, the drive assisting functions include functions for fully automated driving, collision control (automatic braking), uniform speed driving (auto-cruising), and lane-keep assisting. In the fully automated driving, acceleration, steering, and braking are all automatically controlled. In the automatic braking, braking is automatically controlled. In the auto-cruising, acceleration and braking are automatically controlled. In the lane-keep assisting, steering is automatically controlled.

More specifically, the function determination unit 203 acquires the identity information of the vehicle 100 from the measuring unit 201, and references function information using the identity information, thereby determining the drive assisting function of the vehicle 100. The function information defines a correspondence relationship between the identity information and the drive assisting function, and may be stored on a storage device (not illustrated). The function determination unit 203 may determine the drive assisting function in accordance with information received from the vehicle 100. Also, the function determination unit 203 determines the drive assisting function by recognizing the type of a sensor mounted on the vehicle 100 from the image of the vehicle 100.

The selecting unit 204 selects the drive assisting information in accordance with the vehicle 100. For example, the selecting unit 204 selects information of multiple vehicles measured by the measuring unit 201, based on a positional relationship between the multiple vehicles that use the infrastructure (multiple vehicles 10 of FIG. 1, for example), and the vehicle 100 (the target vehicle 10A of FIG. 1, for example). Alternatively, the selecting unit 204 may select the drive assisting information in accordance with the drive assisting function of the vehicle 100 determined by the function determination unit 203.

The selecting unit 204 may select information of a vehicle having a positional relationship with the vehicle 100 corresponding to the drive assisting function of the vehicle 100, out of information of multiple vehicles using the infrastructure. More specifically, if the function determination unit 203 determines a collision control function, the selecting unit 204 selects information of the vehicle 100 and a vehicle positioned ahead of the vehicle 100 within a first threshold range from the vehicle 100, out of the information of the multiple vehicles using the infrastructure. If the function determination unit 203 determines a fully automated driving function, the selecting unit 204 selects information of the vehicle 100 and a vehicle positioned within the circle having a radius of a second threshold range from the vehicle 100, out of the information of the multiple vehicles using the infrastructure. The first threshold range and the second threshold range may be empirically determined in advance.

Referring to FIG. 1, if the drive assisting function of the target vehicle 10A is the auto-braking function or the auto-cruise function, the selecting unit 204 selects the position information and velocity information of the target vehicle 10A and the vehicle positioned ahead of the target vehicle 10A within the first threshold range (the forward vehicle 10B) out of the information of the multiple vehicles 10. If the drive assisting function of the target vehicle 10A is the lane-keep assisting function, the selecting unit 204 selects, from the drive assisting information, the position information of the target vehicle 10A and the position information of the border line of the lane in which the target vehicle 10A is running. If the drive assisting function of the target vehicle 10A is the fully automated driving function, the selecting unit 204 selects, from the drive assisting information, the position information and velocity information of the target vehicle 10A and the vehicle that is present within the circle having a radius of the second threshold range from the target vehicle 10A (namely, the forward vehicle 10B and the backward vehicle 10C), the position information of the border line between the lanes, map information, and traffic control information.

The transmitting unit 205, including a radio communication adapter, for example, transmits a variety of information to the vehicle 100 via radio communication. More specifically, the transmitting unit 205 transmits to the vehicle 100 the drive assisting information selected by the selecting unit 204.

The receiving unit 206, including a radio communication adapter, for example, and receives a variety of information from the vehicle 100 via radio communication. More specifically, the receiving unit 206 receives from the vehicle 100 the information of the infrastructure measured by the vehicle 100.

The inspecting unit 207 inspects the infrastructure using the information of the infrastructure received from the vehicle 100. In other words, the inspecting unit 207 inspects the infrastructure using the information measured by the vehicle 100. The inspecting unit 207 may combine the information of the infrastructure received from the vehicle 100 and the information of the infrastructure received from another vehicle, and may inspect the infrastructure using the combined information. In this case, the inspecting unit 207 may combine these pieces of information in view of accuracy of the information.

The indicating unit 208 indicates to the vehicle 100 the measurement point where the information of the infrastructure is measured. More specifically, the indicating unit 208 transmits to the vehicle 100 via the transmitting unit 205 a message indicating the measurement point. The measurement point may be determined in view of a necessity for the measurement point of the inspecting unit 207. For example, the measurement point may be a location where the oldest inspection is performed. Alternatively, the measurement point may be a location where a fault is likely to occur.

Operation of Infrastructure Inspection System

Figure 3:
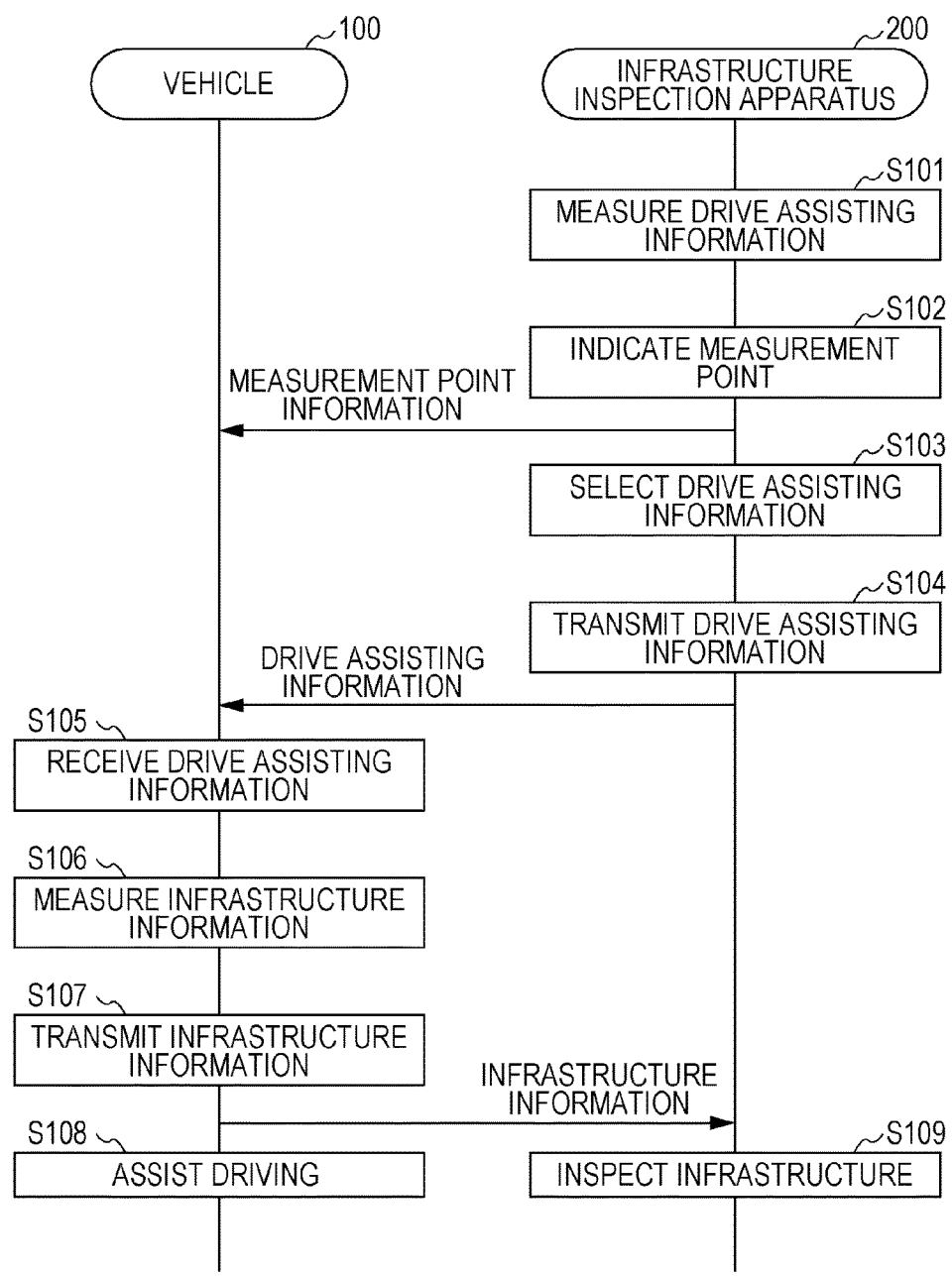
FIG. 3 is a sequence chart of the infrastructure inspection system of the embodiment.

The operation of the infrastructure inspection system 1000 thus constructed is described with reference to FIG. 3. FIG. 3 is a sequence chart of the infrastructure inspection system 1000 of the embodiment.

The infrastructure inspection apparatus 200 measures the drive assisting information that is used for the drive assisting operation of the vehicle 100 that uses the infrastructure (S101). Referring to FIG. 1, the sensor 21 measures the identity information, position and speed of each of the multiple vehicles 10 running in the tunnel 30.

The infrastructure inspection apparatus 200 indicates the measurement point to the vehicle 100 included in the multiple vehicles that use the infrastructure (S102). The measurement point information indicating the measurement point is transmitted from the infrastructure inspection apparatus 200 to the vehicle 100. Referring to FIG. 1, the server 20 transmits to the target vehicle 10A the measurement point information indicating a position in the wall surface 31 of the tunnel 30.

The infrastructure inspection apparatus 200 selects the drive assisting information (S103). For example, referring to FIG. 1, the server 20 selects, from the information of the multiple vehicles 10, information of the target vehicle 10A and the forward vehicle 10B that is running ahead of the target vehicle 10A.

The infrastructure inspection apparatus 200 transmits to the vehicle 100 the selected drive assisting information (S104), and the vehicle 100 receives the selected drive assisting information from the infrastructure inspection apparatus 200 (S105). For example, if the information of the target vehicle 10A and the forward vehicle 10B is selected as illustrated in FIG. 1, the server 20 transmits the position information and velocity information of the target vehicle 10A and the forward vehicle 10B to the target vehicle 10A.

The vehicle 100 measures the information of the infrastructure at the measurement point indicated by the infrastructure inspection apparatus 200 (S106). Referring to FIG. 1, the target vehicle 10A captures an image of the indicated measurement point in the wall surface 31 of the tunnel 30.

The vehicle 100 transmits the information of the measured infrastructure to the infrastructure inspection apparatus 200 (S107). The vehicle 100 performs the drive assisting operation in response to the drive assisting information received from the infrastructure inspection apparatus 200 (S108). For example, referring to FIG. 1, the target vehicle 10A controls acceleration, steering, and braking on the target vehicle 10A in response to the information received from the server 20.

On the other hand, the infrastructure inspection apparatus 200 inspects the infrastructure using the information of the infrastructure received from the vehicle 100 (S109). For example, referring to FIG. 1, the server 20 detects a crack or a water leak in the wall surface 31 from the image of the wall surface 31 of the tunnel 30 received from the target vehicle 10A. Also, the server 20 may detect a distortion of the wall surface or a fault in the wall surface from the stereo image of the wall surface 31 of the tunnel 30.

Operation of each apparatus is described below.

Operation of Vehicle

Figure 4:
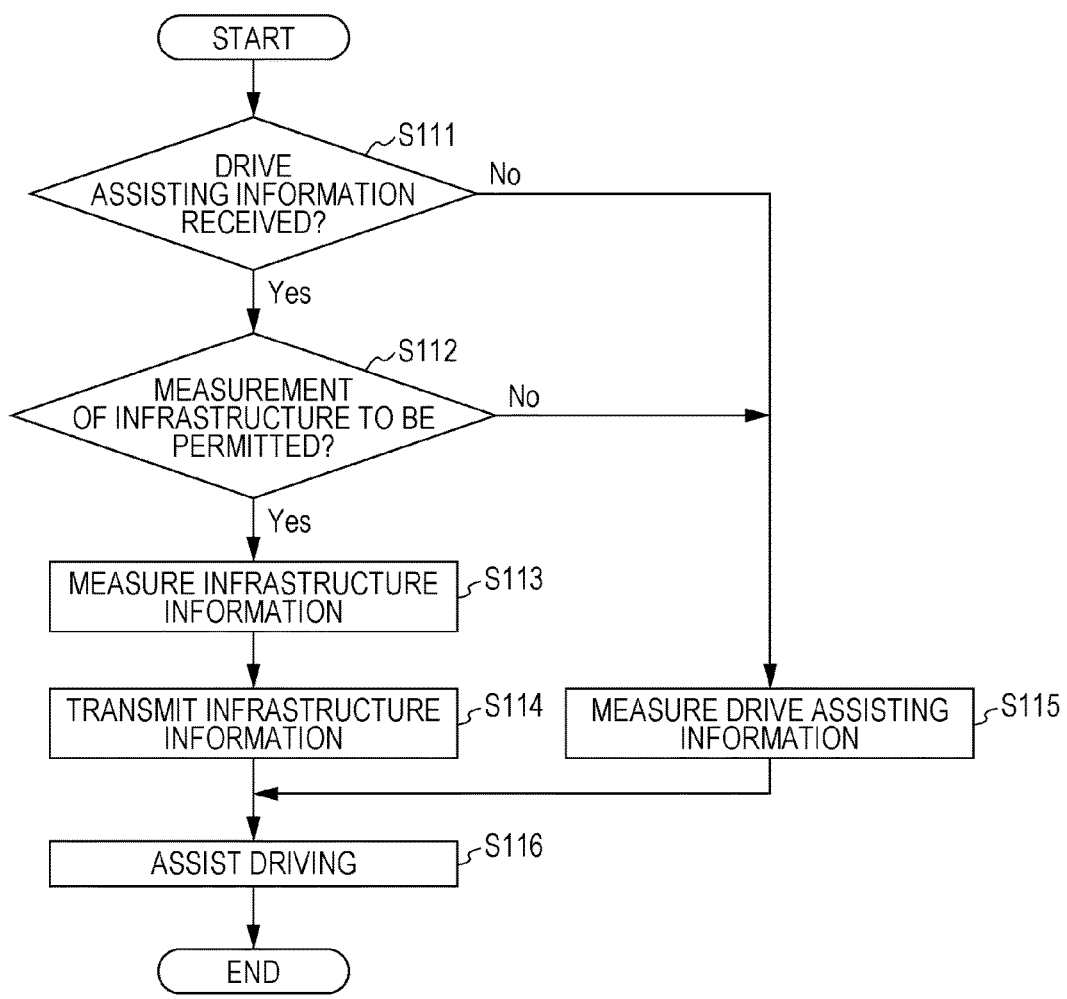
FIG. 4 is a flowchart illustrating an operation of a vehicle of the embodiment.

The operation of the vehicle 100 is described with reference to FIG. 4. FIG. 4 is a flowchart illustrating the operation of the vehicle 100 of the embodiment.

The receiving unit 101 determines whether the drive assisting information has been received from the infrastructure inspection apparatus 200 (S111). If the receiving unit 101 has received the drive assisting information from the infrastructure inspection apparatus 200 (yes branch from S111), the determination unit 102 determines whether to permit the infrastructure to be measured (S112).

If the measurement of the infrastructure is to be permitted (yes branch from S112), the measuring unit 103 measures the information of the infrastructure (S113). The transmitting unit 104 transmits the information of the measured infrastructure to the infrastructure inspection apparatus 200 (S114).

If the receiving unit 101 has not received the drive assisting information from the infrastructure inspection apparatus 200 (no branch from S111), or the measurement of the infrastructure is not permitted (no branch from S112), the measuring unit 103 measures the drive assisting information (S115).

Finally, the drive assisting unit 105 performs the drive assisting operation of the vehicle 100 in accordance with the drive assisting information received from the infrastructure inspection apparatus 200 (the second drive assisting information) or the drive assisting information measured by the measuring unit 103 (the first drive assisting information) (S116).

Operation of Infrastructure Inspection Apparatus

Figure 5:
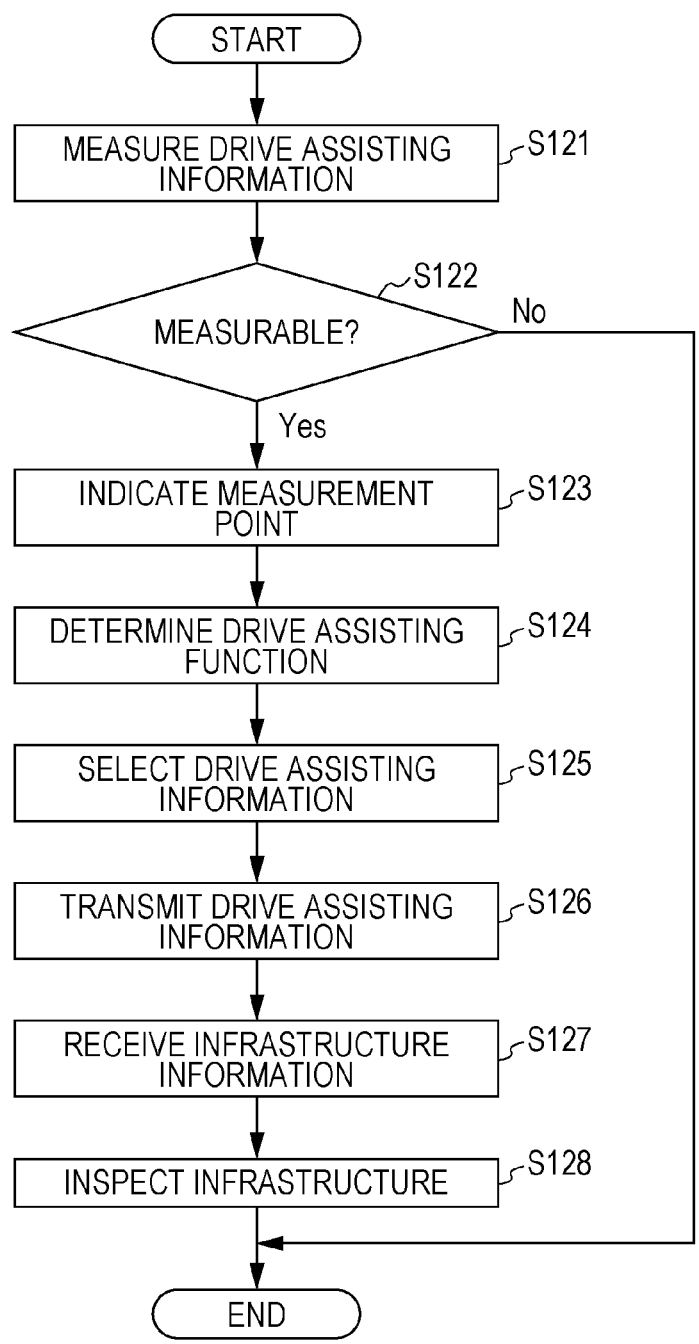
FIG. 5 is a flowchart illustrating an operation of an infrastructure inspection apparatus of the embodiment.

The operation of the infrastructure inspection apparatus 200 is described with reference to FIG. 5. FIG. 5 is a flowchart illustrating an operation of the infrastructure inspection apparatus 200 of the embodiment.

The measuring unit 201 measures the drive assisting information for use in the drive assisting operation on the vehicle 100 that uses the infrastructure (S121).

The measuring capability determination unit 202 determines whether the vehicle 100 is capable of measuring the information of the infrastructure (S122). If the vehicle 100 is not capable of measuring the information of the infrastructure (no branch from S122), the operation of the infrastructure inspection apparatus 200 ends.

If the vehicle 100 is capable of measuring the information of the infrastructure (yes branch from S122), the indicating unit 208 indicates the measurement point to the vehicle 100 (S123). The function determination unit 203 determines the drive assisting function of the vehicle 100 (S124).

The selecting unit 204 selects the drive assisting information, based on the determined drive assisting function (S125).

The transmitting unit 205 transmits the selected drive assisting information to the vehicle 100 (S126). The receiving unit 206 receives from the vehicle 100 the information of the infrastructure at the indicated measurement point (S127).

The inspecting unit 207 inspects the infrastructure using the received information of the infrastructure (S128).

Advantages

The vehicle 100 of the embodiment has the drive assisting function. The vehicle 100 includes the measuring unit 103, the transmitting unit 104, the receiving unit 101, and the drive assisting unit 105. The measuring unit 103 measures the information of the infrastructure used by the vehicle 100, and the first drive assisting information used for the drive assisting operation of the vehicle 100. The transmitting unit 104 transmits the information of the infrastructure to the infrastructure inspection apparatus 200 when the measuring unit 103 measures the information of the infrastructure. The receiving unit 101 receives the second drive assisting information from the infrastructure inspection apparatus 200. The drive assisting unit 105 performs the drive assisting operation on the vehicle 100 in accordance with the first drive assisting information measured by the measuring unit 103 i) when the measuring unit 103 measures the first drive assisting information, or performs the drive assisting operation on the vehicle 100 in accordance with the second drive assisting information received by at least the receiving unit 101 ii) when the measuring unit 103 measures the information of the infrastructure.

When the information of the infrastructure is measured, the vehicle 100 is capable of receiving the second drive assisting information from the infrastructure inspection apparatus 200. The vehicle 100 is thus capable of receiving from the infrastructure inspection apparatus 200 the drive assisting information that the vehicle 100 is short of when the vehicle 100 measures the information of the infrastructure. Since the vehicle 100 is capable of transmitting the information of the infrastructure to the infrastructure inspection apparatus 200, the infrastructure is measured using the information of the infrastructure measured by the vehicle 100.

In the vehicle 100 of the embodiment, the receiving unit 101 may receive from the infrastructure inspection apparatus 200 the indication of the measurement point to measure the information of the infrastructure, and the measuring unit 103 may measure the information of the infrastructure at the measurement point.

Information of a location appropriate for the inspection of the infrastructure is thus measured, leading to an efficient inspection.

In the vehicle 100 of the embodiment, the drive assisting unit 105 may perform the drive assisting operation of the vehicle 100 in response to the measurement point.

The vehicle 100 may be guided to the location that is appropriate for the measurement, and the information of the infrastructure is effectively measured.

In the vehicle 100 of the embodiment, the measuring unit 103 may selectively perform the measurement modes including the first measurement mode to measure the drive assisting information and the second measurement mode to measure the information of the infrastructure.

Switching is thus made between the first measurement mode with the drive assisting operation having a higher priority and the second measurement mode with the measurement of the information of the infrastructure having a higher priority.

In the vehicle 100 of the embodiment, the measuring unit 103 measures a range within a predetermined sector from the vehicle 100. The center direction of the sector may be aligned with the direction to the front of the vehicle 100 in the first measurement mode, and the center direction of the sector may be shifted from the direction to the front of the vehicle 100 to the direction to the infrastructure in the second measurement mode.

The mode may be switched from the first measurement mode to the second measurement mode by changing a measurement direction of the range of the range finder.

In the vehicle 100 of the embodiment, the measuring unit 103 measures a range within the circle centered on the vehicle 100. In the second measurement mode, the measurement accuracy in the direction to the infrastructure may be higher than the measurement accuracy in other directions.

Effective information for the inspection of the infrastructure is thus obtained in the second measurement mode.

The vehicle 100 of the embodiment further includes the determination unit 102 that determines whether to permit the information of the infrastructure to be measured. If the measurement of the information of the infrastructure is permitted, the measuring unit 103 measures the information of the infrastructure. If the measurement of the information of the infrastructure is not permitted, the measuring unit 103 may measure the first drive assisting information.

If the measurement of the information of the infrastructure is not permitted, a decrease in the drive assisting capability is controlled by measuring the information of the infrastructure.

The infrastructure inspection apparatus 200 of the embodiment is thus used to inspect the infrastructure that is used by vehicles. The infrastructure inspection apparatus 200 includes the measuring unit 201 that measures the drive assisting information for use in the drive assisting operation of the vehicle 100 using the infrastructure, the transmitting unit 205 that transmits the drive assisting information to the vehicle 100, the receiving unit 206 that receives from the vehicle 100 the information of the infrastructure measured by the vehicle 100, and the inspecting unit 207 that inspects the infrastructure using the information of the infrastructure.

The infrastructure inspection apparatus 200 is capable of transmitting to the vehicle 100 the drive assisting information for use in the drive assisting operation of the vehicle 100. The infrastructure inspection apparatus 200 is capable of providing to the vehicle 100 the drive assisting information that the vehicle 100 is short of when the vehicle 100 measures the information of the infrastructure. The infrastructure inspection apparatus 200 thus controls a decrease in the drive assisting capability of the vehicle 100 caused by measuring the infrastructure. Using the information of the infrastructure measured by the vehicle 100, the infrastructure inspection apparatus 200 inspects the infrastructure. The infrastructure inspection apparatus 200 thus inspects the infrastructure at lower cost with higher frequency.

The infrastructure inspection apparatus 200 of the embodiment further includes the selecting unit 204 that selects the drive assisting information in accordance with the vehicle 100. The transmitting unit 205 may transmit the selected drive assisting information to the vehicle 100.

The infrastructure inspection apparatus 200 may select the drive assisting information and may thus transmit to the vehicle 100 the drive assisting information with unwanted information removed therefrom. The amount of communication between the infrastructure inspection apparatus 200 and the vehicle 100 is reduced, and the work load on the vehicle 100 is also reduced.

The infrastructure inspection apparatus 200 of the embodiment further includes the function determination unit 203 that determines the drive assisting function of the vehicle 100. The selecting unit 204 may select the drive assisting information, based on the determined drive assisting function.

The infrastructure inspection apparatus 200 may transmit to the vehicle 100 information appropriate for the drive assisting function of the vehicle 100. This restricts the transmission of the unwanted information that is not used by the vehicle 100, and the amount of communication is reduced.

In the infrastructure inspection apparatus 200 of the embodiment, the drive assisting information includes information of multiple vehicles that use the infrastructure. The selecting unit 204 may select information of a vehicle that has a positional relationship with the vehicle 100 corresponding to the drive assisting function of the vehicle 100.

The infrastructure inspection apparatus 200 may transmit to the vehicle 100 information more appropriate for the drive assisting function of the vehicle 100.

The infrastructure inspection apparatus 200 of the embodiment further includes the measuring capability determination unit 202 that determines whether the vehicle 100 is capable of measuring the information of the infrastructure. If the vehicle 100 is capable of measuring the information of the infrastructure, the transmitting unit 205 may transmit the drive assisting information to the vehicle 100.

The infrastructure inspection apparatus 200 may transmit the information to the vehicle 100 only when the information of the infrastructure is likely to be received from the vehicle 100. The work load on the infrastructure inspection apparatus 200 is thus reduced.

The infrastructure inspection apparatus 200 of the embodiment may include the indicating unit 208 that indicates to the vehicle 100 the measurement point where the information of the infrastructure is to be measured.

Since the measurement point is indicated, the information of the infrastructure is effectively collected.

In the infrastructure inspection apparatus 200 of the embodiment, the drive assisting information may include at least the position information or the velocity information of each of one or more vehicles that use the infrastructure.

The infrastructure inspection apparatus 200 may thus transmit the information more appropriate for the drive assisting operation of the vehicle 100.

Modifications

The vehicle, the infrastructure inspection apparatus, and the infrastructure inspection system, related to one more aspects of the disclosure have been discussed with reference to the embodiment. The disclosure is not limited to the embodiment. Modifications of the embodiment easily realized by those of ordinary skill in the art may fall within the scope of one or more aspects of the disclosure as long as the modifications do not depart from the scope of the disclosure.

In the embodiment, the infrastructure is a tunnel. The infrastructure is not limited to the tunnel. The infrastructure may be any infrastructure used by vehicles. For example, the infrastructure may be a road or a bridge.

The vehicle 100 and the infrastructure inspection apparatus 200 do not necessarily have to include all the elements described above. For example, the vehicle 100 may not necessarily have to include the determination unit 102. In such a case, the measurement of the information of the infrastructure is considered to be usually permitted. The infrastructure inspection apparatus 200 may at least include the measuring unit 201, the transmitting unit 205, the receiving unit 206, and the inspecting unit 207. If the selecting unit 204 or the like is not included, all the drive assisting information measured by the measuring unit 201 may be simply transmitted to the vehicle 100. If the identity information of the vehicle is included in the drive assisting information, the vehicle 100 discriminates information of the host vehicle from information of another vehicle.

In accordance with the embodiment, an element that is not closely related to the inspection of the infrastructure and the drive assisting operation of the vehicle is not particularly described. The vehicle 100 and the infrastructure inspection apparatus 200 may include another element. For example, the vehicle 100 includes an engine and tires.

In accordance with the embodiment, the selecting unit 204 selects the drive assisting information, based on the drive assisting function of the vehicle 100. Alternatively, the drive assisting information may be selected regardless of the drive assisting function. In such a case, for example, the selecting unit 204 may select, from the information of multiple vehicles, information concerning a vehicle positioned within a predetermined range from the vehicle 100. The selecting unit 204 may acquire the identity information of the vehicle 100 from the measuring unit 201, acquire information for selection corresponding to the identity information, and select the drive assisting information using the information for selection. In this case, the identity information of the vehicle and the information for selection may be stored in association with each other on a storage device (not illustrated).

Some or all elements included in the vehicle 100 and the infrastructure inspection apparatus 200 of the embodiment may be implemented by a single large scale integration (LSI) or multiple dedicated electronic circuits. For example, the determination unit 102 and the drive assisting unit 105 in the vehicle 100 may be implemented by a system LSI or multiple dedicated electronic circuits. The determination unit 102 and the drive assisting unit 105 in the vehicle 100 may be implemented by a processor that executes instructions or a software program stored on a non-transitory memory. Similarly, the measuring capability determination unit 202, the function determination unit 203, the selecting unit 204, and the inspecting unit 207 in the infrastructure inspection apparatus 200 may be implemented by a single LSI or multiple dedicated electronic circuits. Alternatively, the measuring capability determination unit 202, the function determination unit 203, the selecting unit 204, and the inspecting unit 207 in the infrastructure inspection apparatus 200 may be implemented by a processor that executes instructions or a software program stored on a non-transitory memory.

The system LSI is a super multi-function LSI that is manufactured by integrating multiple modules on a single chip. More specifically, the system LSI is a computer including a micro-processor, a read-only memory (ROM), and a random-access memory (RAM). The ROM stores a computer program. The LSI performs the function thereof when the microprocessor operates in accordance with the computer program.

The system LSI has been described herein. Depending on the difference in the degree of integration, the system LSI is referred to as IC, LSI, super LSI, or ultra LSI. The technique of integration is not limited to the LSI. The system LSI may be implemented by a dedicated circuit or a general-purpose processor. A field programmable gate array (FPGA) that is programmable after the manufacture of the LSI may be used, or a reconfigurable processor that enables circuit cell connection and setting within the LSI to be reconfigured may be used.

If an integration technique replacing the LSI technique emerges as the semiconductor technology advances or as a result of creation of another technique, functional blocks may be integrated using such an integration technique. The use of biotechnology is contemplated as one option.

An aspect of the embodiment of the disclosure is related to not only the vehicle 100 and the infrastructure inspection apparatus 200, but also a measurement method and an infrastructure inspection method, each of which includes, as steps, characteristic elements included in the vehicle 100 and the infrastructure inspection apparatus 200. Another aspect of the embodiment of the disclosure may be related to a computer program that causes a computer to perform the characteristic steps included in the measurement method and the infrastructure inspection method. Another aspect of the embodiment of the disclosure may be related to a non-transitory computer-readable recording medium that has recorded the computer program thereon.

In accordance with each of the embodiment and the modifications thereof, each element may be implemented by dedicated hardware, or may be implemented by executing the software program adapted to each element. Each of the elements may be implemented when a central processing unit (CPU) or a processor reads and then executes the software program stored on a recording medium, such as a hard disk or a semiconductor memory.

The disclosure is applicable as an infrastructure inspection apparatus and a vehicle, each of which is used to inspect an infrastructure, such as a tunnel.

What is claimed is:

1. An inspection apparatus comprising:
   a sensor that measures drive assisting information that is used to perform a drive assisting operation of a target vehicle that uses an infrastructure;
   a transmitter that transmits the drive assisting information to the target vehicle;
   a receiver that receives, from the target vehicle, information of the infrastructure measured by the target vehicle; and
   circuitry which performs operations, the operations including:
   inspecting the infrastructure using the received information of the infrastructure; and
   determining whether the target vehicle is capable of measuring the information of the infrastructure, wherein the transmitter transmits the drive assisting information to the target vehicle if the target vehicle is capable of measuring the information of the infrastructure.

2. The inspection apparatus according to claim 1, wherein the operations further include selecting the drive assisting information in response to the target vehicle, and
   wherein the transmitter transmits the selected drive assisting information to the target vehicle.

3. The inspection apparatus according to claim 2, wherein the operations further include determining a drive assisting function of the target vehicle, and
   wherein the selecting is performed based on the determined drive assisting function.

4. The inspection apparatus according to claim 3, wherein the drive assisting information comprises information concerning a plurality of vehicles that use the infrastructure, and wherein the selecting includes selecting, from the information concerning the vehicles, information concerning a vehicle that corresponds to the determined drive assisting function and has a predetermined positional relationship with the target vehicle.

5. The inspection apparatus according to claim 1, wherein the sensor is mounted in the infrastructure.

6. The inspection apparatus according to claim 1, wherein the operations further include indicating to the target vehicle a measurement point where the information of the infrastructure is to be measured.

7. The inspection apparatus according to claim 1, wherein the drive assisting information comprises at least position information or velocity information of at least one vehicle that uses the infrastructure.

8. An inspection system comprising a vehicle and an inspection apparatus,
wherein the vehicle includes:
a first sensor that measures information of an infrastructure used by the vehicle and first drive assisting information used to perform a driving assisting operation of the vehicle;
a first transmitter that transmits, to the inspection apparatus, the information of the infrastructure when the first sensor has measured the information of the infrastructure;
a first receiver that receives, from the inspection apparatus, second drive assisting information used to perform the drive assisting operation of the vehicle when the first sensor has measured the information of the infrastructure; and
circuitry which performs operations, the operations including:
performing the drive assisting operation of the vehicle in response to the first drive assisting information when the first sensor has measured the first drive assisting information; and
performing the drive assisting operation of the vehicle in response to the second drive assisting information when the first sensor has measured the information of the infrastructure; and
wherein the inspection apparatus includes:
a second sensor that measures the second drive assisting information;
a second transmitter that transmits the second drive assisting information to the vehicle;
a second receiver that receives from the vehicle the information of the infrastructure measured by the vehicle; and
circuitry which performs operations, the operations including inspecting the infrastructure using the received information of the infrastructure.

9. An inspection method comprising:
with a sensor mounted in an infrastructure, measuring drive assisting information that is to be used to perform a drive assisting operation of a target vehicle that uses the infrastructure;
determining whether the target vehicle is capable of measuring the information of the infrastructure;
transmitting the drive assisting information to the target vehicle if the target vehicle is capable of measuring the information of the infrastructure;
receiving, from the target vehicle, information of the infrastructure measured by the target vehicle; and
inspecting the infrastructure using the information of the infrastructure.

* * * * *